United States Patent
Potoček et al.

(10) Patent No.: US 9,762,863 B2
(45) Date of Patent: Sep. 12, 2017

(54) METHOD OF SAMPLING A SAMPLE AND DISPLAYING OBTAINED INFORMATION

(71) Applicant: FEI Company, Hillsboro, OR (US)

(72) Inventors: Pavel Potoček, Eindhoven (NL); Martinus Petrus Maria Bierhoff, Deurne (NL); Tomáš Vystavěl, Brno (CZ); Lukáš Drybčák, Brno (CZ)

(73) Assignee: FEI Company, Hillsboro, OR (US)

( * ) Notice: Subject to any disclaimer, the term of this patent is extended or adjusted under 35 U.S.C. 154(b) by 603 days.

(21) Appl. No.: 14/090,215

(22) Filed: Nov. 26, 2013

(65) Prior Publication Data
US 2014/0146160 A1    May 29, 2014

Related U.S. Application Data

(60) Provisional application No. 61/730,330, filed on Nov. 27, 2012.

(30) Foreign Application Priority Data
Nov. 27, 2012   (EP) ..................................... 12194321

(51) Int. Cl.
*H04N 7/18*    (2006.01)
*G01N 23/225*    (2006.01)
(Continued)

(52) U.S. Cl.
CPC ........... *H04N 7/18* (2013.01); *G01N 23/2251* (2013.01); *H01J 37/265* (2013.01); *H01J 37/28* (2013.01)

(58) Field of Classification Search
CPC .... G01N 23/2251; H01J 37/265; H01J 37/28; H04N 7/18
(Continued)

(56) References Cited

U.S. PATENT DOCUMENTS 8,232,523 B2    7/2012   Boughorbel et al.
2011/0164110 A1*  7/2011   Fortin ................ H04N 13/0048
                                                      348/43
(Continued)

FOREIGN PATENT DOCUMENTS

EP              2584363 A1    4/2013
JP              2002323463    11/2002
JP    WO 2011089911 A1 *   7/2011    ............ H01J 37/265

OTHER PUBLICATIONS

"JP 2002-323463 Translation". Nov. 2008.*
(Continued)

*Primary Examiner* — Zhihan Zhou
(74) *Attorney, Agent, or Firm* — Scheinberg & Associates, P.C.; Michael O. Scheinberg

(57) ABSTRACT

The invention relates to a method of sampling and displaying information comprising scanning a beam over the sample in a series of N overlapping sub-frames, each comprising $M_n$ scan positions, thereby irradiating the sample at N×$M_n$ scan positions, which form the field of view;

Figure 1:
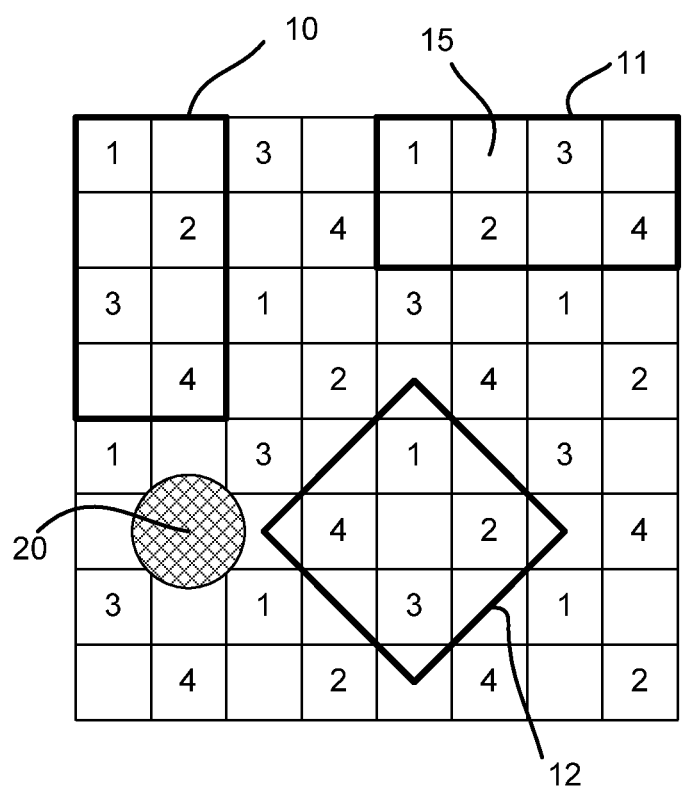

detecting a signal, sampled for each scan position, emanating from the sample; and displaying the sub-frames having at least N×$M_n$ pixels in such a way, that after the series of N scans each of the pixels displays information derived from the signal from one or more scan positions;

in which after the scan of the first sub-frame each of the pixels displays information derived from the scan positions of the first sub-frame; and after the scan of the second sub-frame each of the pixels displays information derived during the scanning of the first, the second, or both sub-frames.

20 Claims, 2 Drawing Sheets

(51) Int. Cl.
*H01J 37/28* (2006.01)
*H01J 37/26* (2006.01)

(58) Field of Classification Search
USPC .......................................... 348/80
See application file for complete search history.

(56) References Cited

U.S. PATENT DOCUMENTS

| | | |
|---|---|---|
| 2012/0287258 A1* | 11/2012 | Tsuneta ................. H01J 37/265 |
| | | 348/80 |
| 2012/0292503 A1 | 11/2012 | Phifer, Jr. et al. |
| 2013/0037714 A1 | 2/2013 | Boughorbel et al. |
| 2013/0037715 A1 | 2/2013 | Boughorbel et al. |
| 2013/0228683 A1 | 9/2013 | Boughorbel et al. |

OTHER PUBLICATIONS

Unknown, Brochure for the Nova NanoSEM, FEI Company: http:www.fei.com/products/scanning-electron0microsdopes/nova-nanosem/nanosenbrochure.aspx, 2013.

Unknown, "Interlace and MPEG—Can motion compensation help?", J.O. Drewery, International Broadcasting Convention 1994 (IBC1994). http://www.bbc.co.uk/rd/pubs/papers/pdffiles/jodibc94.pdf.

Unknown, "Nova NanoSEM Superior Imaging and Analytical Performance" http://labsoft.pl/wordpress/wp-content/uploads/2013/08/FEI_NovaNanov2_R4M_091812.pdf, obtained May 2013, 12 pages.

* cited by examiner

METHOD OF SAMPLING A SAMPLE AND DISPLAYING OBTAINED INFORMATION

The invention relates to a method of sampling a sample and displaying obtained information on a display, the method comprising:

Scanning a beam over the sample in a series of N overlapping sub-frames, one sub-frame at a time, each sub-frame comprising $M_n$ scan positions, the scan positions of each sub-frame not overlapping with the scan positions of other sub-frames, the beam thereby irradiating the sample at $N \times M_n$ scan positions, the $N \times M_n$ scan positions forming the field of view;

Using a detector detecting a signal emanating from the sample in response to the irradiation of the sample by said beam, said signal sampled for each scan positions; and Displaying the sub-frames on the display having at least $N \times M_n$ pixels in such a way, that after the series of N scans each of the pixels displays information derived from the signal from one or more scan positions;

Such a method is known from the interlaced scanning used in the Nova NanoSEM Scanning electron microscope from FEI Company, Hillsboro, USA, that is equipped to scan with an interlaced raster.

In a Scanning Electron Microscope (SEM) a focused beam of electrons with a selectable energy of for example between 200 eV and 30 keV is scanned over a sample. In response to the electron beam impinging on the sample radiation emerges from the sample, the radiation including Secondary Electrons (SEs) with an energy of less than 50 eV, Backscattered Electrons (BSEs) with an energy in excess of 50 eV, light, and X-rays. One or more of these types of radiation can be sampled/detected by a detector.

The scan pattern can be a continuous scan pattern, or an interlaced scan pattern. The advantage of an interlaced scan pattern is, according to a brochure of the Nova NanoSEM (see [—1—], more specifically page 7, "user interface") that, as an area of interest is scanned quicker (although more often), interlaced scanning allows for the charge to dissipate before rescanning the area of interest (albeit at slightly different scan positions), and thus achieves optimal charge-free imaging.

It is noted that a better charge distribution and dissipation can also be achieved by scanning faster using a smaller dwell time (the time that the beam is at one position), combined by e.g. integrating or averaging of the images. However, a disadvantage of this is that not all detectors are capable of the resulting fast sample times (the detector not having sufficient bandwidth), or show a deterioration of their signal-to-noise ratio. Also some physical phenomena related to the sample can be time restrained, such as the observance of fluorescence: fluorescence has a long decay time and is thus not suited to detect by fast sampling.

Such a method is also known from the sampling/display scheme of MUSE (MUltiple sub-Nyquist Sampling Encoding) analog HDTV.

In MUSE a sampling scheme as shown in FIG. 1 is used, see also "Interlace and MPEG—Can motion compensation help", J. O. Drewery. International Broadcasting Convention 1994 (IBC1994) [-2-].

A number of four sub-frames is defined, each sub-frame containing scan positions and corresponding pixels on the display (television screen) that are here denoted with "1", "2", "3" and "4" respectively.

First the first sub frame is scanned, transmitted and displayed, then the second sub-frame, etc. A complete image is thus formed after the transmittal of 4 sub-frames. As with interlaced scanning/transmittal this lowers flickering of the images. The frames are typically transmitted with a frame rate of 15 Hz (thus a sub-frame rate of 60 Hz). After displaying the $4^{th}$ sub-frame of the $1^{st}$ series of sub-frames, the $1^{st}$ sub-frame of the $2^{nd}$ image is displayed. This can be achieved by changing the information in a memory cell that is part of an image memory, or it can e.g. be achieved by directing an electron beam to a fluorescent screen with a controlled current to the position of the corresponding pixel.

The invention offers an improved scanning/imaging method.

To that end after the scan of the first sub-frame each of the pixels displays information derived from the scan positions of the first sub-frame; and after the scan of the second sub-frame each of the pixels displays information derived during the scanning of the first sub-frame, the second sub-frame, or both sub-frames.

Already after the first sub-frame an image is displayed using all pixels, and thus with the correct overall contrast/brightness levels. The information thus obtained can be used for a first quick image using all pixels, but the same information is also used in subsequent images, with subsequent higher resolution.

It is noted that already in the first image, but also in subsequent images, e.g. interpolation techniques may be used to enhance the resolution as displayed It is further noted that for one group of prior art methods, until all N sub-frames are scanned, only part of the pixels show information while the rest of the pixels is black, leading to an image with a wrong overall brightness level until all sub-images are scanned.

In other prior art methods, until all N sub-frames are scanned, part of the pixels showed outdated information, relating to, for example, information sampled while the sample was at another position, or the detector was at other settings, leading to an image that, at least in part, showed wrong contrast, brightness, or positional information.

Admittedly, for HDTV this is not an important issue, as after 4 sub-frames a complete image is present, and each time a new sub-frame is displayed it replaces an old sub-frame. This all happens so fast, that after a start-up of ¹/₁₅ of a second (¹/₁₅ of a second being the frame rate) all pixels are in use all the time, and are refreshed with new information after each frame.

For, for example, a SEM the scan time is variable, typically showing a frame rate of 25 Hz to once per second or even less, e.g. once per minute. Using a scan time resulting in a frame rate of $1 \text{ s}^{-1}$, it is useful to observe a low-resolution image in a fraction of the time, so that, for example, it can be decided whether the field of view (the imaged area) contains an interesting feature. The following sub-frames will then contribute to a higher resolution, after which further sub-frames can be used to improve the signal-to-noise ratio of the image.

In an embodiment the number of scan positions and pixels per sub-frame is identical for all sub-frames.

Preferably the number of scan positions and pixels per sub-frame is identical for all sub-frames, but this is not necessary. One or more sub-frames may, for example, miss a row and/or column of scan positions.

In an embodiment of the invention $N=(k_x \times k_y)$, with $k_x$ and $k_y$ a positive integer, at least one of $k_x$ and $k_y$ larger than 1, more specifically $N=k^2$, with k an integer larger than 1.

By choosing $N=(k_x \times k_y)$, with $k_x$ and $k_y$ a positive integer the corresponding pixels of the different sub-frames can be grouped in a rectangle, and by N=k² the corresponding pixels of the different sub-frames can be grouped in a square.

In another embodiment of the invention the beam is a beam from the group of infrared light, visible light or X-rays, or a beam of particles from the group of electrons, ions, charged clusters, charged molecules, atoms or molecules.

Although the invention is explained using a SEM, the invention can also be used with an apparatus using another beam than an electron beam.

In yet another embodiment of the invention at least one of the series of N sub-frames the position of the sub-frame with respect to one or more of the other sub-frames is corrected for drift and/or vibration of the sample.

By comparing different sub-frames, a shift between the images can be detected by, for example, correlation techniques. A detected drift can then be compensated for, either by simply shifting the data obtained when displaying it, or by more elaborate techniques as described in, for example, pending European Patent Application EP12188958, or "A Fast Super Resolution Algorithm for SEM Image", L. Hengshu, Proc. of SPIE Vol. 6623 66231Z [-3-].

In yet another embodiment of the invention a new sequence of sub-frames is started after displacement larger than a predetermined value is detected between the last obtained sub-frame and at least one of earlier obtained sub-frames.

In this embodiment the display of a new sequence of N sub-frames is started as soon as a displacement larger than a predetermined value is detected between the last obtained sub-frame and at least one of earlier obtained sub-frames. The displacement may be due to a change in sample position, and then results in a low-resolution image while a stage on which the sample is mounted is moving, and resulting in a high-resolution image (using all sub-frames) when the stage become stationary.

In yet another embodiment of the invention a user can initiate the start of a new sequence of sub-frames, or a new sequence of sub-frames is started after a movement of a sample stage on which the sample is mounted, or a new sequence of sub-frames is started after a movement of a sample stage on which the sample is mounted, a change of the field of view, or a change in detector settings.

Especially for low refresh rates and high numbers of N, the time it takes to build a new image is long. It is then attractive to start the build of a new image (a new sequence of sub-frames) by either a user request or automatically after a movement of a stage on which a sample is mounted. By "flushing the buffer" a new image is started.

In yet another embodiment of the invention after the scan of the first sub-frame at least part of the pixels show information derived from two or more scan positions.

When the first sub-frame is scanned a first image is displayed, using the information of the first sub-frame. However, by interpolation between the information obtained from two or more scan positions, an image with improved virtual resolution can be displayed. Even when the data of more sub-frames is imaged, interpolation can be attractive, and when all N sub-frames are sampled, an image with so-called super-resolution can be displayed, assuming that the display has more than N×M pixels.

In yet another embodiment of the invention the detector detects the number and/or energy and/or angular distribution of X-ray photons, light photons, secondary electrons or backscattered electrons emanating from the sample.

The detector detecting the radiation emanating from the sample may be an X-ray detector (using EDX or WDX as detecting principle), a photon detector (for example a Si-PMT, a PMT, a photodiode, or a CMOS or CCD detector), an SE detector (for example a Everhart-Thornley detector, or a semiconductor detector), a BSE detector (for example a semiconductor detector), a detector for electrons transmitted through a sample (such as an energy less spectrometer), and many more.

In a preferred embodiment of the invention the scan time of each sub-frame is identical to the scan time of each other sub-frame.

Scan time for the different sub-frames need not be identical, but in most cases this is the easiest choice.

Figure 2:
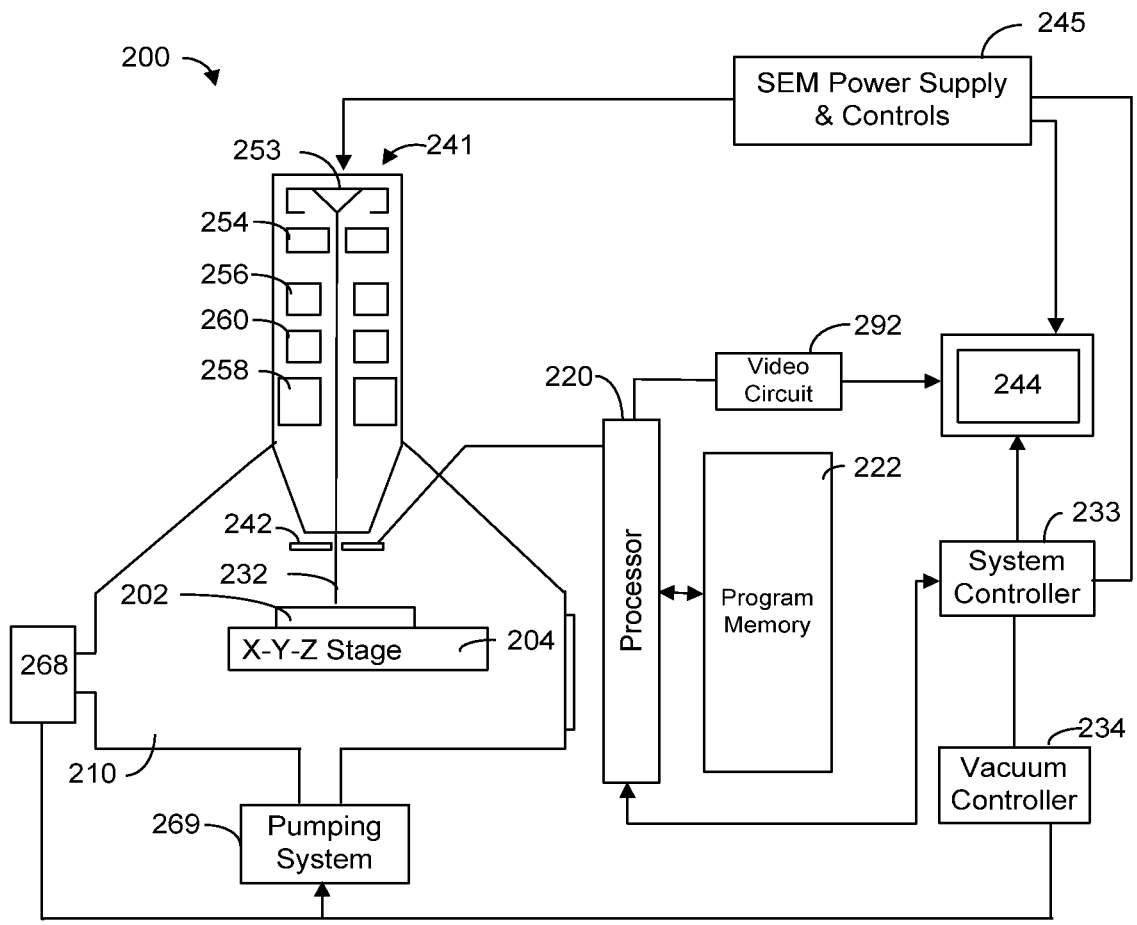

The invention is now elucidated using figure, in which identical reference numerals indicate corresponding features. To that end:

FIG. 1 schematically shows the scanning strategy used in MUSE;

FIG. 2 schematically shows a SEM.

FIG. 1 schematically shows the scanning strategy used in MUSE.

In MUSE a frame consists of 4 sub-frames. Each sub-frame is displaced with respect to the other sub-frames. The 1$^{st}$ sub-frame consists of the scan positions marked "1", and displays these scan positions on the corresponding positions of a display. Likewise the second sub-frame consists of the scan positions marked "2", and displays these scan positions on the corresponding positions of a display, etc. Analog to crystallography, several "unit-cells" can be defined, such as unit-cell 10, unit-cell 11 and unit-cell 12. Each of these cells contains one scan position of each of the N sub-frames with a minimum of displacement. Especially the diamond shaped unit cell 12 is suited to use as a cell to fill the complete image of N-sub-frames, although its orientation is such that it is unlikely to fit the image of N*M scan positions, as such images often show straight edges.

The MUSE scan scheme shows many unscanned areas 15. As can be seen in the unit-cells, only half of the area of the sample is scanned, resulting in undersampling (not sampling all the area of the sample). To avoid undersampling a slightly oversized spot 20 can be used to scan the image. This lowers the undersampling, although (depending on the diameter of the spot and the scan raster) it may lead to a slight oversampling, where one sample contains information of other scan positions as well.

FIG. 2 schematically shows a SEM equipped to perform the method according to the invention.

FIG. 2 shows an apparatus 200 with a scanning electron microscope column 241, along with power supply and control unit 245. An electron beam 232 is emitted from a cathode 253 by applying voltage between cathode 253 and an anode 254. Electron beam 232 is focused to a fine spot by means of a condensing lens 256 and an objective lens 258. Electron beam 232 is scanned two-dimensionally on the specimen by means of a deflection coil 260. The deflector coils can deflect the beam along the x-axis and along the y-axis so that the beam can be scanned along a sample surface in a simple or complex pattern, such as a raster scan, serpentine scan, or a Hilbert scan. Deflectors can be magnetic or electrostatic. Operation of condensing lens 256, objective lens 258, and deflection coil 260 is controlled by power supply and control unit 245.

A system controller 233 controls the operations of the various parts of the apparatus 200. The vacuum chamber 210 is evacuated with ion pump 268 and mechanical pumping system 269 under the control of vacuum controller 234.

Electron beam 232 can be focused onto sample 202, which is on a movable X-Y stage 204 within vacuum chamber 210. When the electrons in the electron beam strike sample 202, the sample gives off radiation. Backscattered electrons are detected by backscattered electron detector 242, preferably a segmented silicon drift detector.

Data processor 220 can comprise a computer processor, programmable gate array, or other digital or analog processing means; operator interface means (such as a keyboard or computer mouse); program memory 222 for storing data and executable instructions; interface means for data input and output, executable software instructions embodied in executable computer program code; and display 244 for displaying the results by way of video circuit 292.

Data processor 220 can be a part of a standard laboratory personal computer, and is typically coupled to at least some form of computer-readable media. Computer-readable media, which include both volatile and nonvolatile media, removable and non-removable media, may be any available medium that can be accessed by data processor 220. By way of example and not limitation, computer-readable media comprise computer storage media and communication media. Computer storage media include volatile and non-volatile, removable and non-removable media implemented in any method or technology for storage of information such as computer-readable instructions, data structures, program modules or other data. For example, computer storage media include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by processor 220.

Also program memory 222 can include such computer storage media in the form of removable and/or non-removable, volatile and/or nonvolatile memory and can provide storage of computer-readable instructions, data structures, program modules and other data.

By loading the program memory with appropriate instructions, the apparatus is equipped to perform the method according to the invention.

It is noted that, although the apparatus discussed here is an apparatus equipped with an electron microscope column, but also apparatuses equipped with a focused ion beam column, a laser beam column, a charged cluster column, etc., may be used, as well as combinations thereof.

It is further noted that the demand for a long dwell time can vary: it may be the result of the sample (for example fluorescence or phosporescense result in long decay time, necessitating log sample times), or the detector (for example as a result of the deterioration of the signal-to-noise ratio when the sampling time is low, or having a limited bandwidth).

Non-Patent Literature

[-1-] Brochure for the Nova NanoSEM, FEI Company: http://www.fei.com/products/scanning-electron-microscopes/nova-nanosem/nanosembrochure.aspx
[-2-] "Interlace and MPEG—Can motion compensation help?", J. O. Drewery, International Broadcasting Convention 1994 (IBC1994). http://www.bbc.co.uk/rd/pubs/papers/pdffiles/jodibc94.pdf
[-3-] "A Fast Super Resolution Algorithm for SEM Image", L. Hengshu, Proc. of SPIE Vol. 6623 66231Z.

We claim as follows:

1. A method of sampling a sample and displaying obtained information on a display, the method comprising:
   scanning a beam over the sample in a series of N overlapping sub-frames of a frame, one sub-frame at a time, each sub-frame comprising $M_n$ scan positions spanning over an entire image area of the frame, except for at least two peripheral pixel areas, and spread over $M_n$ sub-cells with each sub-cell having a scan position for each sub-frame, the scan positions of each sub-frame not overlapping with the scan positions of other sub-frames, the beam thereby irradiating the sample at $N \times M_n$ scan positions, the $N \times M_n$ scan positions forming a field of view;
   using a detector detecting a signal emanating from the sample in response to the irradiation of the sample by said beam, said signal sampled for each of the $N \times M_n$ scan positions; and
   displaying the sub-frames on the display using at least $N \times M_n$ pixels in such a way that after the series of N scans, each of the at least $N \times M_n$ pixels displays information derived from the signal from one or more of the $N \times M_n$ scan positions;
   in which:
      after the scan of the first sub-frame each of the at least $N \times M_n$ pixels displays information derived from one or more scan positions of the first sub-frame and at least part of the at least $N \times M_n$ pixels show interpolated information derived from two or more scan positions of the first sub-frame; and
      after the scan of the second sub-frame each of the at least $N \times M_n$ pixels displays information derived during the scanning of the first sub-frame, the second sub-frame, or both sub-frames.

2. The method of claim 1 in which the number of scan positions and pixels per sub-frame is identical for all sub-frames.

3. The method of claim 1 in which $N=(k_x \times k_y)$, with $k_x$ and $k_y$ a positive integer, at least one of $k_x$ and $k_y$ larger than 1, more specifically $N=k^2$, with k an integer larger than 1.

4. The method of claim 1 in which the beam is a beam from the group of infrared light, visible light or X-rays, or a beam of particles from the group of electrons, ions, charged clusters, charged molecules, atoms or molecules.

5. The method of claim 1 in which for at least one of the series of N sub-frames the position of the sub-frame with respect to one or more of the other sub-frames is corrected for drift and/or vibration and/or displacement of the sample.

6. The method of claim 1 in which a new sequence of sub-frames is started after displacement larger than a predetermined value is detected between the last obtained sub-frame and at least one of earlier obtained sub-frames.

7. The method of claim 1 in which a user can initiate the start of a new sequence of sub-frames, or a new sequence of sub-frames is started after a movement of a sample stage on which the sample is mounted, a change of the field of view, or a change in detector settings.

8. The method of claim 1 in which the detector detects the number and/or energy and/or angular distribution of X-ray photons, light photons, secondary electrons or backscattered electrons emanating from the sample.

9. The method of claim 1 in which a scan time of each sub-frame is identical to a scan time of each other sub-frame.

10. The method of claim 1 wherein, within each sub-cell, the scan positions for each sub-frame are offset from the each other such that no two scan positions are adjacent side-by-side or adjacent top-to-bottom.

11. A charged-particle apparatus comprising:
   a charged particle source for producing a charged particle beam;

a sample holder for holding and positioning a sample;

a charged-particle lens system for directing said beam through the sample;

a detector for detecting a signal emanating from the sample in response to the irradiation of the sample by the beam; and a system controller including a program memory for storing machine readable instructions for:

scanning the beam over the sample in a series of N overlapping sub-frames of a frame, one sub-frame at a time, each sub-frame comprising $M_n$ scan positions spanning over an entire image area of the frame, except for at least two peripheral pixel areas, and spread over $M_n$ sub-cells with each sub-cell having a scan position for each sub-frame, the scan positions of each sub-frame not overlapping with the scan positions of other sub-frames, the beam thereby irradiating the sample at $N \times M_n$ scan positions, the $N \times M_n$ scan positions forming a field of view;

using the detector to detect a signal emanating from the sample in response to the irradiation of the sample by the beam, said signal sampled for each of the $N \times M_n$ scan positions; and displaying the sub-frames on the display using at least $N \times M_n$ pixels in such a way that after the series of N scans, each of the at least $N \times M_n$ pixels displays information derived from the signal from one or more of the $N \times M_n$ scan positions;

in which:

after the scan of the first sub-frame each of the at least $N \times M_n$ pixels displays information derived from one or more scan positions of the first sub-frame and at least part of the at least $N \times M_n$ pixels show interpolated information derived from two or more scan positions of the first sub-frame; and after the scan of the second sub-frame each of the at least $N \times M_n$ pixels displays information derived during the scanning of the first sub-frame, the second sub-frame, or both sub-frames.

12. The charged particle apparatus of claim 11 in which the number of scan positions and pixels per sub-frame is identical for all sub-frames.

13. The charged particle apparatus of claim 11 in which $N=(k_x \times k_y)$, with $k_x$ and $k_y$ a positive integer, at least one of $k_x$ and $k_y$ larger than 1, more specifically $N=k^2$, with k an integer larger than 1.

14. The charged particle apparatus of claim 11 in which the beam is a beam from the group of infrared light, visible light or X-rays, or a beam of particles from the group of electrons, ions, charged clusters, charged molecules, atoms or molecules.

15. The charged particle apparatus of claim 11 in which for at least one of the series of N sub-frames the position of the sub-frame with respect to one or more of the other sub-frames is corrected for drift and/or vibration and/or displacement of the sample.

16. The charged particle apparatus of claim 11 in which a new sequence of sub-frames is started after displacement larger than a predetermined value is detected between the last obtained sub-frame and at least one of earlier obtained sub-frames.

17. The charged particle apparatus of claim 11 in which a user can initiate the start of a new sequence of sub-frames, or a new sequence of sub-frames is started after a movement of a sample stage on which the sample is mounted, a change of the field of view, or a change in detector settings.

18. The charged particle apparatus of claim 11 in which the detector detects the number and/or energy and/or angular distribution of X-ray photons, light photons, secondary electrons or backscattered electrons emanating from the sample.

19. The charged particle apparatus of claim 11 in which a scan time of each sub-frame is identical to a scan time of each other sub-frame.

20. The apparatus of claim 11 wherein, within each sub-cell, the scan positions for each sub-frame are offset from the each other such that no two scan positions are adjacent side-by-side or adjacent top-to-bottom.

* * * * *